United States Patent [19]

Biermans et al.

[11] Patent Number: 4,572,830

[45] Date of Patent: Feb. 25, 1986

[54] PROCESS FOR DETERMINING AND CONTROLLING THE COMPOSITION OF AQUEOUS SOLUTIONS OF NH3 AND CO2

[75] Inventors: Andreas J. Biermans, Urmond; Henk C. Burks, Oirsbeek, both of Netherlands

[73] Assignee: Unie van Kunstmestfabrieken B.V., Utrecht, Netherlands

[21] Appl. No.: 564,884

[22] Filed: Dec. 23, 1983

[30] Foreign Application Priority Data

Dec. 24, 1982 [NL] Netherlands ............ 8204979

[51] Int. Cl.⁴ ........................................ F27B 15/08
[52] U.S. Cl. .................................. 423/659; 436/19; 436/52; 436/113
[58] Field of Search ............ 423/659; 422/61, 62, 422/68; 436/19, 52, 113, 146, 816

[56] References Cited

U.S. PATENT DOCUMENTS 3,940,440  2/1976  Mavrovic ............ 260/555 A
3,957,868  5/1976  Verstegen et al. ...... 260/555 A

OTHER PUBLICATIONS

Edward W. Washburn, Editor-in-Chief, International Critical Tables of Numerical Data, Physics, Chemistry and Technology, McGraw-Hill Book Company Inc., NY, 1928, vol. IV, p. 219, vol. III, p. 62.

*Primary Examiner*—John Doll
*Assistant Examiner*—Jackson Leeds
*Attorney, Agent, or Firm*—Cushman, Darby & Cushman

[57] ABSTRACT

A process for determining the composition of an aqueous solution of ammonia and carbon dioxide from which ammonium carbamate or ammonium carbonate crystallizes out upon cooling to below the saturation temperature. The density and the saturation temperature of the solution are measured, and the ammonia, carbon dioxide, and water composition is determined by reference to densities and saturation temperatures of aqueous solutions of ammonia and carbon dioxide of known composition. The composition thus determined can be used to effect control over the composition of such aqueous solutions.

4 Claims, 2 Drawing Figures

4,572,830

PROCESS FOR DETERMINING AND CONTROLLING THE COMPOSITION OF AQUEOUS SOLUTIONS OF NH₃ AND CO₂

BACKGROUND OF THE INVENTION

The invention relates to a process for determining the composition of aqueous solutions of $NH_3$ and $CO_2$ from which ammonium carbamate or ammonium carbonate.$H_2O$ (ammonium carbonate with one water of crystallization) crystallizes out upon cooling to below the saturation temperature. In the following discussion, reference will be made only to ammonium carbamate, which term should be understood to include also ammonium carbonate.

Such solutions occur in practice as process streams in, for example, the preparation of urea and/or the preparation of melamine. In the preparation of urea, to obtain optimum conversion in the synthesis zone it is necessary that the water content of carbamate solutions to be recirculated to this zone should be kept as low as possible while still preventing carbamate from crystallizing out. To achieve this objective, the composition of such a process stream must be know. Thus far, various methods of analysis have been used to analyze such solutions. However, these methods have been difficult to apply in that the method of analysis used is too slow to permit timely corrective measures in the event of deviations from the correct composition. The object of the present invention is to provide a process for determining the composition of such solutions in which process the aforementioned difficulties are overcome.

SUMMARY OF THE INVENTION

It has now been found that, within the range of composition relevant to the practical applications indicated, the composition of an aqueous solution of $NH_3$ and $CO_2$ is fully determined if both the density and the saturation temperature thereof are known. If, on the basis of experimental data obtained from solutions of known composition, a set of saturation isotherms (lines of constant saturation temperature) and a set of lines of constant density are plotted in, for instance, a triangular diagram of $NH_3$—$CO_2$—$H_2O$ concentrations, the lines of the two sets will intersect. By interpolation between these two sets of lines, it will then be possible to quickly determine the composition of any such solution sample by means of only its measured density and saturation temperature, and any necessary process corrections can be expeditiously carried out. This has been found to be applicable to compositions roughly defined by the following limiting relations (the percentages indicated are percentages by weight):

% $NH_3 < 60\%$   (1)

$7 > \%\ NH_3/CO_2 > 0.75$   (2)

% $H_2O < 65\% + 0.75 \cdot \%\ CO_2$   (3)

The process according to the invention is therefore characterized in that the density and the saturation temperature of the solution are measured, and the percentages of $NH_3$, $CO_2$, and $H_2O$ are determined on the basis of densities and saturation temperatures measured with respect to solutions of known composition.

The density of a given solution depends to some extent on its temperature and must, consequently, be measured at a certain standard temperature, for instance 100° C. If so desired, a density measured at a deviating temperature can be corrected to obtain the value at the standard temperature.

Equipment for determining the densities of liquids, such as the said solutions, is commercially available. Very suitable for this application are, for instance, vibration-type densimeters, wherein the liquid being examined is passed through a tube which is vibrated, and the density of the liquid can be determined by the frequency of vibration.

If the crystalline phase is ammonium carbamate, preference is given, for determining the saturation temperature, to the use of a process and device as described in co-pending U.S. application Ser. No. 515,502 filed on July 20, 1983. In that process, the temperature of the solution is gradually raised in an optical measuring vessel from a temperature at wnhich the solution contains crystals of the dissolved substance to a temperature at which all crystals are dissoved. While the temperature is being raised and constantly measured, a beam of light is passed through the measuring vessel and the dissolution of the last few crystals present is detected optically. The beam of light is a plane-polarized beam of light and the transmitted beam of light is passed through an analyser, the polarization direction of which is perpendicular to that of the light beam. The intensity of the light passing through the analyser is measured with a photometer, and the saturation temperature is determined at the moment when this intensity has reached a low, substantially constant value. For the generation of the plane-polarized light beam, preference is given in using a laser. In the measuring cycle, a solution not containing any crystals is generally first fed to the measuring vessel, the temperature of the measuring vessel is gradually lowered until crystals are formed, and the temperature of the measuring vessel is subsequently gradually raised until the crystals dissolve.

Owing to the use of polarized light, the detection method exclusively responds to the formation or disappearance of optically active crystals, such as ammonium carbamate crystals. Optically nonactive particles, such as most solid impurities, therefore, do not or hardly disturb the measurement.

If the phase crystallizing out is ammonium carbonate.$H_2O$, the above-described method for determining the saturation temperature cannot be used, because ammonium carbonate.$H_2O$ crystals are cubic and consequently not optically active. In that case, one of the known other methods must be used to measure the saturation temperature.

The invention also relates to a process for controlling the composition of an aqueous solution of $NH_3$ and $CO_2$ from which ammonium carbamate or ammonium carbonate.$H_2O$ would crystallize out upon cooling to below the saturation temperature. This process is characterized in that the density and the saturation temperature of the solution are measured, the percentages of $NH_3$, $CO_2$, and $H_2O$ are determined by reference of these measured properties against densities and saturation temperatures of solutions of known composition, and the $H_2O$ content is controlled in relation thereto by the supply of water or of an aqueous solution.

This improved control procedure can be advantageously applied in the processing of solutions containing ammonium carbamate solutions and/or ammonium carbonate formed in the preparation of urea from $NH_3$ and $CO_2$ and/or in the preparation of melamine from urea.

The invention can be applied in a process for the preparation of urea, preferably in the following manner. After removal of most of the non-converted ammonium carbamate from the synthesis solution formed in the urea synthesis zone, the remaining urea solution, still containing ammonium carbamate, is separated in a low-pressure zone into an aqueous urea solution and a gas mixture containing $NH_3$, $CO_2$, and $H_2O$. This gas mixture is condensed, and the ammonium carbamate solution obtained is recirculated to the urea synthesis zone, together with a portion of relatively dilute aqueous solution obtained by condensing the gas mixtures given off during concentration of the aqueous urea solution. The composition of the recirculated ammonium carbamate solution is determined by measurement of its density and saturation temperature as above described, and adjusted in response thereto as necessary to maintain the desired composition by adding an appropriate quantity of the relatively dilute aqueous solution. In this process the ratio of the percentages of $NH_3$ and $CO_2$, determined on the basis of the solution density and saturation temperature as above described, can also be controlled by the addition of $NH_3$ at the value desired for condensation under optimum conditions.

The process of the invention can also be advantageously applied in processes for the preparation of melamine from urea. The gas mixture leaving the reactor, after the melamine is separated out, consists mainly of $NH_3$ and $CO_2$. In one such process known in the art, an aqueous solution is formed containing the $NH_3$ and $CO_2$ in at least partly bonded form as ammonium carbamate or ammonium carbonate. This solution is usually passed to a urea synthesis plant after the water content has been reduced to a value sufficiently low to minimize its impact on the urea synthesis efficiency, but not so low that crystallization of ammonium carbamate or ammonium carbonate might occur. The composition and water content of this solution can be quickly determined by, and timely regulated in response to, measurement of its density and saturation temperature in accordance with the invention as described above.

BRIEF DESCRIPTION OF THE DRAWINGS

The invention is elucidated with reference to the drawings in which the figures represent the following.

DESCRIPTION OF THE PREFERRED EMBODIMENTS

Figure 1:
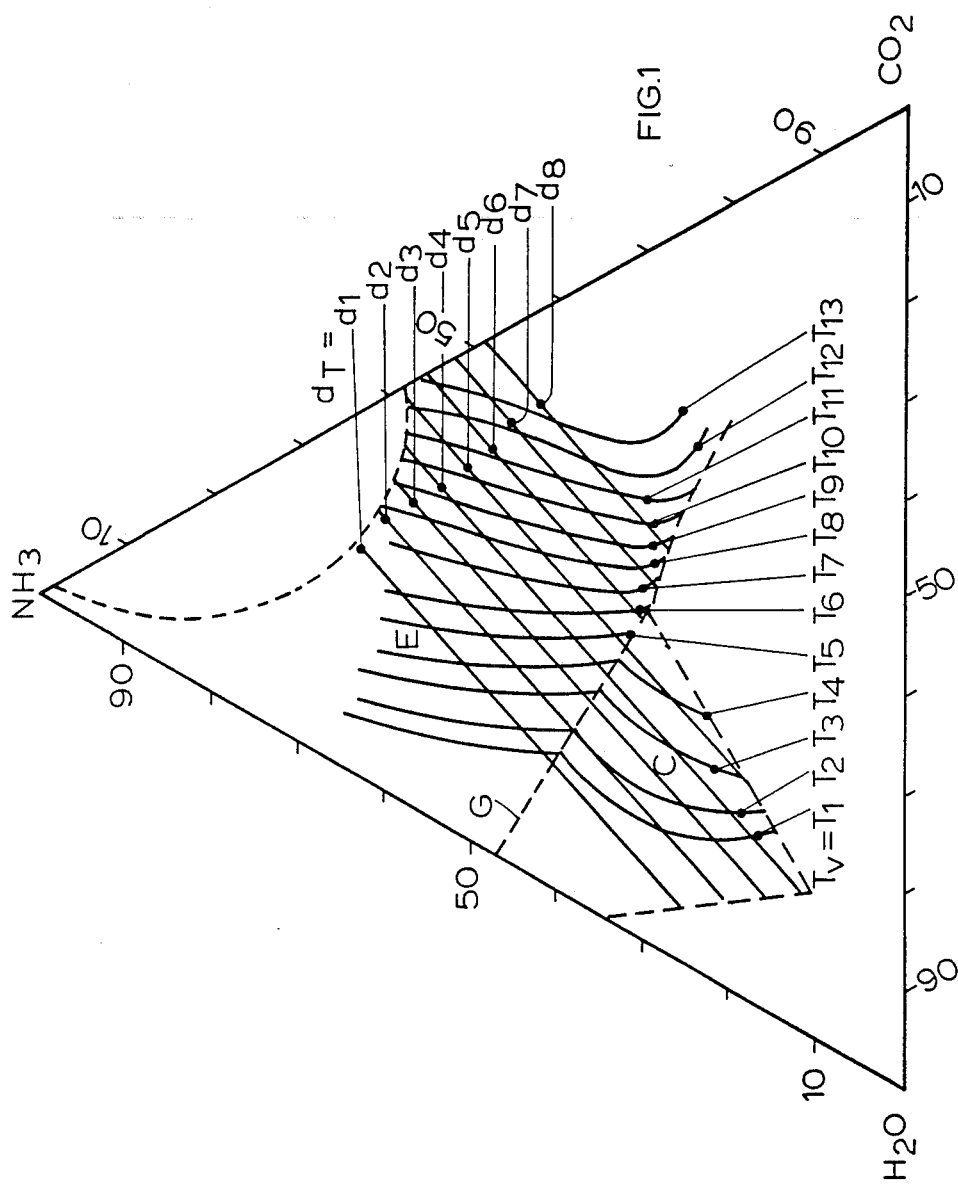
FIG. 1 is an illustrative triangular diagram of $NH_3$—$CO_2$—$H_2O$ solution concentrations with saturation isotherms and lines of constant density indicated therein.

FIG. 1 illustrates the representation of the data base of experimentally determined values on a triangular diagram. In FIG. 1 the coordinates of the triangular diagram show the composition in percent by weight of a solution containing $NH_3$, $CO_2$, and $H_2O$. In the diagram, lines of constant saturation temperature $T_v = T_1$ up to an including $T_{13}$ (saturation isotherms) and lines of constant density at a standard temperature of T°C., $d_T = d_1$ up to and including $d_8$ are indicated. The families of lines $T_v$ and $d_T$ are a diagrammatical representation of lines determined experimentally from solutions of known composition. In the diagram, E indicates the composition range in which ammonium carbamate crystallizes out during cooling and C indicates the range in which ammonium carbonate.$H_2O$ crystallizes out. The dashed line G indicates the boundary line between ranges E and C. If the values of $T_v$ and $d_T$ of an aqueous solution of $NH_3$ and $CO_2$ have been measured, the composition can be determined by interpolation in the diagram. This data base of values determined by experiment can also be stored in the memory of a microprocessor, and the processor can be programmed with an algorithm which determines the composition of an unknown solution from its measured values $T_v$ and $d_T$ by interpolation between the experimental values stored in the memory.

Figure 2:
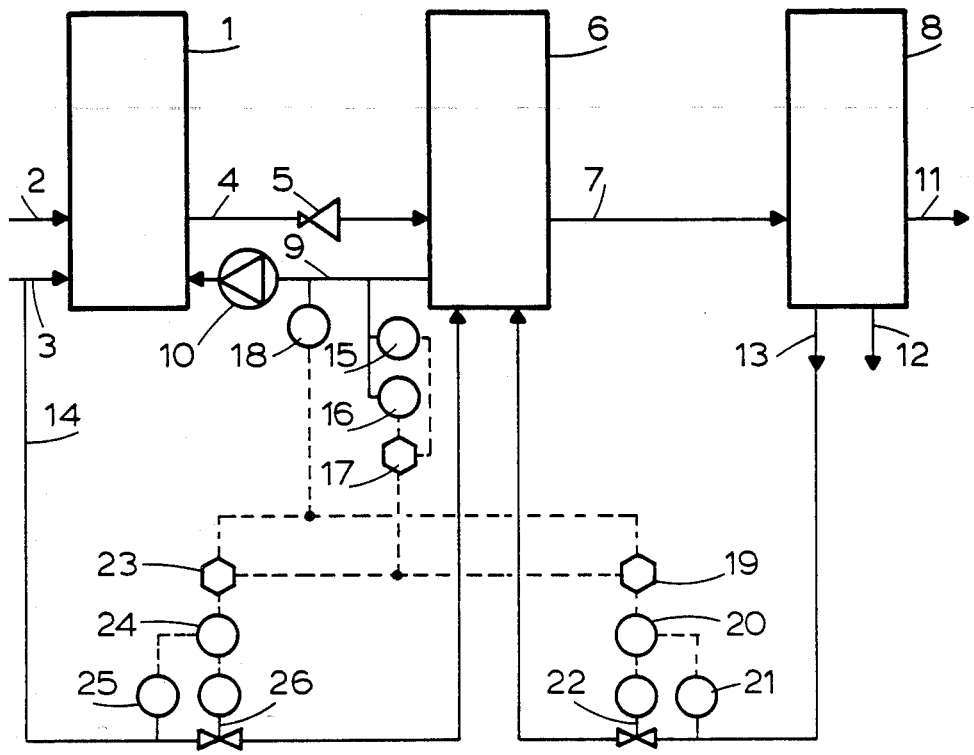
FIG. 2 is a highly simplified schematic diagram of part of a urea plant indicating how, by means of the process according to the invention, the composition of a certain process stream can be monitored and controlled.

FIG. 2 represents a highly simplified block diagram of a urea plant in which the process according to the invention is applied, and will be described by way of a non-restrictive example.

Block 1 represents the high-pressure synthesis section of the plant, to which $CO_2$ is supplied through line 2 and $NH_3$ through line 3. In synthesis section 1 a urea synthesis solution is obtained, containing, in addition to urea and water, non-converted $CO_2$ and $NH_3$, partly in bonded form as ammonium carbamate. This synthesis solution is fed through line 4 via reducer 5, in which the pressure of the solution is lowered from, for instance, 10–20 MPa to, for instance, 0.2–2 MPa, to the low-pressure section of the plant represented by block 6. In this low-pressure section, carbamate is decomposed and $NH_3$ and $CO_2$ are removed from the synthesis solution, and the aqueous urea solution thus obtained is supplied through line 7 to the final processing section of the plant represented by block 8. The $NH_3$ and $CO_2$ removed in the low-pressure stage are condensed and the resulting aqueous solution of $CO_2$ and $NH_3$ (substantially bonded in the form of ammonium carbamate) is recirculated through line 9 to the high-pressure synthesis section 1 by means of pump 10, with which the recirculated solution is brought to the high synthesis pressure again.

In the final processing section 8, the urea is separated from water by evaporation of the solution supplied through line 7, usually granulated and carried off at 11 as finished product. The water separated from the urea is largely condenced to process condensate. Part of this process condensate is carried off from the process threeugh line 12, another part is recirculated through line 3 to low-pressure section 6 and used to lower the concentration of the ammonium carbamate solution recirculated through line 9 to synthesis section 1. Without this measure, the said solution would often be so concentrated that crystallization might occur, for instance in line 9 or pump 10, which is undesirable in view of the danger of clogging. However, the amount of process condensate recirculated through line 13 must not exceed what is required for the certain prevention of this crystallization, because the addition of water will reduce the urea synthesis efficiency in section 1 and all the water added must, moreover, be evaporated again.

Furthermore, extra $NH_3$ is preferably supplied to low-pressure section 6 through line 14 in order to bring the $NH_3/CO_2$ ratio of the solution recirculated through line 9 to the desired value.

For regulating the quantity of process condensate recirculated through line 13 and the quantity of $NH_3$ supplied through line 14 the process according to the invention is used as follows.

The density of the solution recirculated through line 9 is measured continuously with a densimeter 15, and the saturation temperature is measured with a saturation-temperature meter 16. The measuring signals of meters 15 and 16 are passed to a digital signal processing unit 17 generating signals corresponding with the $NH_3$ and $CO_2$ content of the recirculating solution. A flow meter 18 measures the quantity of recirculating solution.

A digital ratio controller 19 receives the measuring signal of flow meter 18 and the analytical signals of the signal processing unit 17 and generates a setting signal for the set-point of flow controller 20, which controls the quantity of process condensate recirculated through line 13. Flow controller 20 receives the measuring signal from a flow meter 21 and controls a control valve 22 in line 13. The quantity of process condensate recirculated through line 13 is set so that the water concentration of the solution recirculated through line 9 to high-pressure section 1 is as low as possible, but not lower than compatible with the certain prevention of the risk of crystallization. To this end, a certain margin must be maintained between the temperature of the solution transported through line 9 and the saturation temperature thereof.

When applying the process according to the present invention, a suitable value for this margin is about 5° C. This is substantially smaller, and thus more favorable, than the margin permissible when the quantity of process condensate to be added to the recirculating solution is determined as previously by means of discontinuous sampling and laboratory analysis of the liquid flowing through line 9 in order to determine the saturation temperature to be expected. This determination of the crystallization temperature by a roundabout way is, like other indirect methods, relatively inaccurate. Thus, in order to be certain that crystallization will not occur during recirculation, a substantially larger quantity of process condensate must be added to the recirculating solution such that the saturation temperature of the solution is about 20° C. lower than temperature prevailing in line 9. In applying the process according to the invention, the saturation temperature itself is measured direct and the temperature margin can be much smaller, so that a substantially smaller quantity of water is returned to the synthesis section.

The quantity of water to be added can be further reduced by adding, if necessary, a controlled quantity of $NH_3$ to the solution in order to attain the $NH_3/CO_2$ molar ratio at which the required water content of the solution is minimum.

The control of the quantity of $NH_3$ supplied through line 14 to low-pressure section 6 is quite analogous to the control of the quantity of recirculated process condensate. Another digital ratio controller 23 also receives the measuring signal from flow meter 18 and the analytical signals of the signal-processing unit 17 and generates a setting signal for the set-point of flow controller 24 controlling the quantity of $NH_3$ supplied through line 14. Flow controller 24 receives the measuring signal from a flow meter 25 and controls a control valve 26 in line 14. The quantity of $NH_3$ supplied through line 14 is set so that the $NH_3/CO_2$ molar ratio of the solution recirculated through line 9 to high-pressure section 1 has a certain optimum value for the process operation in high-pressure section 1, which value is usually between 2.0 and 2.2. The addition of $NH_3$ through line 14 is much smaller than the main $NH_3$ supply through line 3, and is usually not more than 2% thereof. In certain cases, the process operation may be such that this addition can be omitted.

What is claimed is:

1. A process for controlling the composition of an aqueous solution of $NH_3$ and $CO_2$ from which ammonium carbamate or ammonium carbonate.$H_2O$ crystallizes out upon cooling to below the saturation temperature, wherein said aqueous solution has an ammonia content of less than about 60% by weight, a weight ratio of ammonia to carbon dioxide in the range of between about 0.75 and 7, and a water content by weight of less than about the sum of 65% plus 0.75 times the weight percent of carbon dioxide, and process comprising the steps of:
   measuring the density and the saturation temperature of said aqueous solution, and correcting said measuring density to a selected standard temperature;
   comparing said mesured corrected density and saturation temperature against a data base derived from predetermined density data at said standard temperature, and from predetermined saturation temperature data for reference aqueous ammonia and carbon dioxide containing solutions having known compositions;
   determining a value corresponding to the known composition of the reference aqueous ammonia and carbon dioxide containing solution having a density and saturation temperature correlating to the correct measured density and saturation temperature of said aqueous solution; and
   adding water to said aqueous solution in an amount adjusted in response to said determined value.

2. The process of claim 1 wherein the ratio of the $NH_3$ and $CO_2$ in said aqueous solution is controlled by the addition of $NH_3$ in an amount adjusted in response to said determined value.

3. The process of claim 1 wherein said corrected density and saturation temperature are compared against a data base of said predetermined density and saturation temperature data represented as a set of saturation isotherms and a set of density isotherms on a triangular diagram of $NH_3$, $CO_2$, and $H_2O$ composition, and said corresponding value is determined by interpolation between said sets of isotherms.

4. The process of claim 1 wherein said corrected density and saturation temperature are compared against a data base stored in the memory of a microprocessor containing said predetermined density and saturation temperature data, and said corresponding value is determined by interpolation of said stored data by means of an algorithm.

* * * * *